US009591896B2

(12) United States Patent
Gilbert et al.

(10) Patent No.: US 9,591,896 B2
(45) Date of Patent: Mar. 14, 2017

(54) METHOD OF MAKING A MECHANICAL FASTENER USING DIVERGING DISKS (71) Applicant: 3M INNOVATIVE PROPERTIES COMPANY, St. Paul, MN (US)

(72) Inventors: Thomas J. Gilbert, St. Paul, MN (US); Pieter J. Gagnon, Minneapolis, MN (US); Mark A. Peltier, Forest Lake, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 63 days.

(21) Appl. No.: 14/401,290

(22) PCT Filed: Mar. 14, 2013

(86) PCT No.: PCT/US2013/031416
§ 371 (c)(1),
(2) Date: Nov. 14, 2014

(87) PCT Pub. No.: WO2013/172957
PCT Pub. Date: Nov. 21, 2013

(65) Prior Publication Data
US 2015/0096659 A1 Apr. 9, 2015

Related U.S. Application Data (60) Provisional application No. 61/647,833, filed on May 16, 2012.

(51) Int. Cl.
*A61F 13/62* (2006.01)
*B32B 38/00* (2006.01)
(Continued)

(52) U.S. Cl.
CPC ...... *A44B 18/0011* (2013.01); *A44B 18/0019* (2013.01); *A44B 18/0069* (2013.01);
(Continued)

(58) Field of Classification Search
CPC ......... B32B 2555/02; B32B 2038/0028; A61F 13/622; A61F 13/625; A61F 13/627;
(Continued)

(56) References Cited

U.S. PATENT DOCUMENTS 3,252,181 A   5/1966   Hureau
3,616,154 A   10/1971  Dow et al.
(Continued)

FOREIGN PATENT DOCUMENTS

EP   0191355   8/1986
EP   0755665   1/1997
(Continued)

OTHER PUBLICATIONS

Supplementary European Search Report for Application No. EP13790553, dated Oct. 12, 2015, one page.
(Continued)

*Primary Examiner* — Carson Gross (57) ABSTRACT

A method of making a mechanical fastener. The method includes providing a slit web having mechanical fastening elements, applying tension to the slit web in the machine direction, and spreading the slit web in the cross-machine direction by directing its side edges over two rotating diverging disks to provide a spread mechanical fastening web. The slit web includes a plurality of interrupted slits that are interrupted by intact bridging regions of the web. The two rotating diverging disks are laterally spaced and have a support surface between them that contacts the slit web during the spreading. The spread mechanical fastening web includes multiple strands of the slit web attached to each other at least at some of the intact bridging regions and separated from each other between at least some of the intact bridging regions.

20 Claims, 6 Drawing Sheets (51) Int. Cl.
*A44B 18/00* (2006.01)
*A61F 13/15* (2006.01)
*A44B 99/00* (2010.01)
*B32B 37/18* (2006.01)
*B29C 55/08* (2006.01)

(52) U.S. Cl.
CPC ........ *A44B 99/00* (2013.01); *A61F 13/15756* (2013.01); *A61F 13/627* (2013.01); *B32B 37/18* (2013.01); *B32B 38/0012* (2013.01); *A61F 13/625* (2013.01); *B29C 55/08* (2013.01); *B32B 2038/0028* (2013.01); *B32B 2555/02* (2013.01); *Y10T 156/10* (2015.01)

(58) Field of Classification Search
CPC ...... A61F 13/15601; A44B 18/0003–18/0019; A44B 18/0046–18/008; B29C 55/08
USPC ........................................................ 604/391
See application file for complete search history.

(56) References Cited

U.S. PATENT DOCUMENTS

| | | | |
|---|---|---|---|
| 3,645,433 A | 2/1972 | Lucas et al. | |
| 3,724,737 A | 4/1973 | Bodnar | |
| 3,985,599 A | 10/1976 | Lepoutre et al. | |
| 3,985,600 A | 10/1976 | Blais | |
| 4,001,366 A | 1/1977 | Brumlik | |
| 4,152,479 A | 5/1979 | Larsen | |
| 4,176,775 A | 12/1979 | Brendemuehl | |
| 4,239,141 A | 12/1980 | Frye | |
| 4,288,884 A | 9/1981 | Bahls | |
| 4,294,240 A | 10/1981 | Thill | |
| 4,560,372 A | 12/1985 | Pieniak | |
| 4,676,784 A | 6/1987 | Erdman | |
| 4,775,310 A | 10/1988 | Fischer | |
| 4,842,794 A | 6/1989 | Hovis et al. | |
| 4,862,565 A | 9/1989 | Damour | |
| 4,925,080 A | 5/1990 | Crouse et al. | |
| 4,969,970 A | 11/1990 | Suzuki | |
| 5,043,036 A * | 8/1991 | Swenson ........... A61F 13/15601 156/160 | |
| 5,077,870 A | 1/1992 | Melbye et al. | |
| 5,207,962 A | 5/1993 | Hovis et al. | |
| 5,232,533 A | 8/1993 | Tani et al. | |
| 5,256,231 A | 10/1993 | Gorman et al. | |
| 5,260,015 A | 11/1993 | Kennedy | |
| 5,290,377 A | 3/1994 | Aihara et al. | |
| 5,308,345 A | 5/1994 | Herrin | |
| 5,397,316 A | 3/1995 | LaVon | |
| 5,419,695 A | 5/1995 | Clegg | |
| 5,461,760 A | 10/1995 | Damour | |
| 5,476,437 A | 12/1995 | Damour | |
| 5,517,737 A | 5/1996 | Viltro et al. | |
| 5,560,793 A * | 10/1996 | Ruscher ........... A61F 13/15601 156/164 | |
| 5,605,729 A | 2/1997 | Mody et al. | |
| 5,611,790 A | 3/1997 | Osborn, III | |
| 5,628,097 A | 5/1997 | Benson et al. | |
| 5,660,666 A | 8/1997 | Dilnik | |
| 5,692,271 A | 12/1997 | Provost | |
| 5,713,881 A | 2/1998 | Rezai | |
| 5,729,878 A | 3/1998 | Kurihara | |
| 5,776,343 A | 7/1998 | Cullen et al. | |
| 5,791,030 A | 8/1998 | Aihara et al. | |
| 5,891,549 A | 4/1999 | Beretta | |
| 5,953,797 A | 9/1999 | Provost et al. | |
| 6,093,870 A | 7/2000 | Carlsson | |
| 6,132,660 A | 10/2000 | Kampfer | |
| 6,146,369 A | 11/2000 | Hartman | |
| 6,190,594 B1 | 2/2001 | Gorman et al. | |
| 6,262,331 B1 | 7/2001 | Nakahata et al. | |
| 6,287,665 B1 | 9/2001 | Hammer | |
| 6,391,420 B1 | 5/2002 | Cederblad | |
| 6,419,667 B1 | 7/2002 | Avalon | |
| 6,481,063 B2 | 11/2002 | Shepard | |
| 6,489,003 B1 | 12/2002 | Levitt | |
| 6,531,207 B1 | 3/2003 | Eaton | |
| 6,554,754 B2 | 4/2003 | VanRens | |
| 6,582,642 B1 | 6/2003 | Buzzell | |
| 6,627,133 B1 | 9/2003 | Tuma | |
| 6,637,128 B2 | 10/2003 | Kuroiwa et al. | |
| 6,835,256 B2 | 12/2004 | Menzies | |
| 6,843,762 B2 | 1/2005 | Munche et al. | |
| 6,984,412 B2 | 1/2006 | Tanaka | |
| 7,001,475 B2 | 2/2006 | Ausen | |
| 7,014,906 B2 | 3/2006 | Tuman | |
| 7,048,818 B2 | 5/2006 | Krantz | |
| 7,048,984 B2 | 5/2006 | Seth | |
| 7,125,400 B2 | 10/2006 | Igaue | |
| 7,198,743 B2 | 4/2007 | Tuma | |
| 7,214,334 B2 | 5/2007 | Jens et al. | |
| 7,219,403 B2 | 5/2007 | Miyamoto | |
| 7,223,314 B2 | 5/2007 | Provost | |
| 7,241,483 B2 | 7/2007 | Ausen | |
| 7,371,302 B2 | 5/2008 | Miyamoto | |
| 7,407,496 B2 | 8/2008 | Petersen | |
| 7,622,180 B2 | 11/2009 | Seth | |
| 7,695,799 B2 | 4/2010 | Cree | |
| 7,855,316 B2 | 12/2010 | Meyer et al. | |
| 7,897,078 B2 | 3/2011 | Petersen | |
| 8,020,262 B2 | 9/2011 | Oertel | |
| 8,889,243 B2 | 11/2014 | Hanschen | |
| 9,138,031 B2 | 9/2015 | Wood | |
| 9,138,957 B2 | 9/2015 | Wood | |
| 9,155,669 B2 | 10/2015 | Petersen | |
| 9,314,962 B2 | 4/2016 | Rothwell | |
| 2002/0112325 A1 | 8/2002 | Keohan | |
| 2003/0008106 A1 | 1/2003 | Guenther | |
| 2003/0130644 A1 | 7/2003 | Baker | |
| 2003/0229326 A1 | 12/2003 | Hovis et al. | |
| 2004/0000041 A1 | 1/2004 | Harashige | |
| 2004/0147890 A1 | 7/2004 | Nakahata et al. | |
| 2004/0209042 A1 | 10/2004 | Peacock | |
| 2004/0261230 A1 | 12/2004 | Neeb | |
| 2004/0261232 A1 | 12/2004 | Kurtz, Jr. | |
| 2005/0123720 A1 | 6/2005 | Suzuki et al. | |
| 2006/0288547 A1 | 12/2006 | Jackson | |
| 2007/0107571 A1 | 5/2007 | Saeki | |
| 2007/0131809 A1 | 6/2007 | Kawashita et al. | |
| 2007/0134489 A1 | 6/2007 | Neugebauer | |
| 2009/0047855 A1 | 2/2009 | Seth et al. | |
| 2009/0294044 A1 * | 12/2009 | Gill ................. A61F 13/15601 156/256 | |
| 2009/0311465 A1 | 12/2009 | De Jong | |
| 2010/0100022 A1 | 4/2010 | Greener | |
| 2010/0179463 A1 | 7/2010 | Greener | |
| 2011/0147475 A1 | 6/2011 | Biegler et al. | |
| 2011/0151171 A1 | 6/2011 | Biegler et al. | |
| 2011/0313389 A1 * | 12/2011 | Wood ................. A44B 18/0065 604/391 | |
| 2012/0011685 A1 | 1/2012 | Rocha | |
| 2012/0086145 A1 | 4/2012 | Nakamura | |
| 2012/0204383 A1 * | 8/2012 | Wood ................. A44B 18/0046 24/306 | |
| 2012/0330266 A1 | 12/2012 | Zonneveld et al. | |
| 2014/0142533 A1 | 5/2014 | Peltier | |
| 2014/0220328 A1 | 8/2014 | Ausen | |
| 2014/0234606 A1 | 8/2014 | Ausen | |
| 2014/0332999 A1 | 11/2014 | Rothwell | |
| 2014/0349062 A1 | 11/2014 | Chandrasekaran | |
| 2014/0349079 A1 | 11/2014 | Chandrasekaran | |
| 2015/0079337 A1 | 3/2015 | Ausen | |
| 2015/0096660 A1 | 4/2015 | Gilbert | |

FOREIGN PATENT DOCUMENTS

| | | |
|---|---|---|
| EP | 2277682 | 1/2011 |
| GB | 821959 | 10/1959 |
| GB | 914489 | 1/1960 |
| GB | 1055963 | 1/1967 |
| GB | 1075487 | 7/1967 |
| GB | 1275541 | 5/1972 |
| GB | 2017485 | 10/1979 |

(56) References Cited

FOREIGN PATENT DOCUMENTS

| JP | 36-16493 | 9/1961 |
|----|----------|--------|
| JP | 39-22059 | 10/1964 |
| JP | 2010-29532 | 2/2010 |
| WO | WO 9402091 | 2/1994 |
| WO | WO 9610481 | 4/1996 |
| WO | WO 2004-091437 | 10/2004 |
| WO | WO 2005-122818 | 12/2005 |
| WO | WO 2011-163020 | 12/2011 |
| WO | WO 2012-112768 | 8/2012 |
| WO | 2013-032683 | 3/2013 |
| WO | WO 2013-052371 | 4/2013 |
| WO | WO 2013-170480 | 11/2013 |
| WO | WO 2014-164242 | 10/2014 |

OTHER PUBLICATIONS

US 5,389,416, Feb. 14, 1995, Mody et al. (withdrawn).
International Search Report for PCT International Application No. PCT/US2013/031416, mailed on Jun. 26, 2013, 3pgs.

\* cited by examiner

METHOD OF MAKING A MECHANICAL FASTENER USING DIVERGING DISKS

CROSS REFERENCE TO RELATED APPLICATIONS

This application is a national stage filing under 35 U.S.C. 371 of PCT/US2013/031416, filed Mar. 14, 2013, which claims priority to U.S. Application No. 61/647,833, filed May 16, 2012, the disclosure of which is incorporated by reference in its entirety herein.

BACKGROUND

Hook and loop fastening systems, where the hook member typically includes a plurality of closely spaced upstanding projections with loop-engaging heads, and the loop member typically includes a plurality of woven, nonwoven, or knitted loops, are useful for providing releasable attachment in numerous applications. For example, hook and loop fastening systems are widely used in wearable disposable absorbent articles to fasten such articles around the body of a person. In typical configurations, a hook strip or patch on a fastening tab attached to the rear waist portion of a diaper or incontinence garment, for example, can fasten to a landing zone of loop material on the front waist region, or the hook strip or patch can fasten to the backsheet (e.g., nonwoven backsheet) of the diaper or incontinence garment in the front waist region. Hook and loop fasteners are also useful for disposable articles such as sanitary napkins. A sanitary napkin typically includes a back sheet that is intended to be placed adjacent to the wearer's undergarment. The back sheet may comprise hook fastener elements to securely attach the sanitary napkin to the undergarment, which mechanically engages with the hook fastener elements.

Some hook members have been made with openings in the backing from which the hooks project. See, e.g., U.S. Pat. No. 4,001,366 (Brumlik) and U.S. Pat. No. 7,407,496 (Peterson) and Int. Pat. Appl. Pub. Nos. WO 2005/122818 (Ausen et al.) and WO 1994/02091 (Hamilton).

Some nonwoven materials have been made with openings. Such nonwovens have been attached to elastics or extensible pleated backings. See, e.g., U.S. Pat. Appl. Pub. No. 2004/0147890 (Nakahata et al.), Int. Pat. Appl. Pub. No. WO 1996/10481 (Abuto et al.), and European Patent No. EP 1066008 B1 (Eaton et al.).

SUMMARY

The present disclosure provides a method of making mechanical fastener using a web process. The mechanical fastener comprises openings made from multiple strands of a slit web having mechanical fastening elements with the strands attached to each other at bridging regions of the web and separated from each other between at least some of the bridging regions. The method includes spreading the slit web in the cross-machine direction by directing its side edges over two rotating diverging disks.

In one aspect, the present disclosure provides a method of making a mechanical fastener. The method includes providing a slit web having mechanical fastening elements, applying tension to the slit web in the machine direction, and spreading the slit web in the cross-machine direction by directing its side edges over two rotating diverging disks to provide a spread mechanical fastening web. The slit web includes a plurality of laterally separated interrupted slits that are interrupted by intact bridging regions of the web. The interrupted slits extend in a first direction not parallel to a cross-machine direction. For at least some adjacent interrupted slits, the intact bridging regions are staggered in a direction transverse to the first direction. The spread mechanical fastening web includes multiple strands of the slit web attached to each other at least at some of the intact bridging regions and separated from each other between at least some of the intact bridging regions. The two rotating diverging disks are laterally spaced and have a support surface between them that contacts the slit web during the spreading. Generally, the support surface also contacts the spread mechanical fastening web. In some embodiments, the support surface is connected to the two rotating diverging disks.

The method according to any of the above aspects allows openings to be provided in the mechanical fastener without wasteful material loss. The degree of spreading of the strands in the methods disclosed herein may be adjusted based upon, for example, the desired appearance, weight, or cost in the final product.

The method disclosed herein may be useful, for example, for making a reticulated mechanical fastening web, laminate, strip, or patch that has a unique and attractive appearance. The openings can provide breathability and flexibility to the mechanical fastener, which may enhance the comfort of the wearer, for example, of an absorbent article comprising the mechanical fastener made by the method disclosed herein. The mechanical fastener also is typically able to cover a relatively large area with a relatively small amount of material, which may lower its cost. Also, because of the large area that may be covered by the mechanical fastener in an absorbent article, the mechanical fastener may provide performance enhancement, for example, by resist shifting forces such as torsional or rotational forces caused by movement of the wearer of the absorbent article. For example, in use, fitting an absorbent article such as a diaper about the wearer usually requires the front and back waist portions of the diaper to overlap each other. As the diaper is worn the movements of the wearer tend to cause the overlapping front and back waist portions to shift position relative to each other. Unless such shifting is limited, the fit and containment characteristics of the diaper may be degraded as the diaper is worn. The mechanical fastener made according to the present disclosure may provide improved fit and closure stability by resisting such shifting because of its relatively larger area and flexibility.

In this application, terms such as "a", "an" and "the" are not intended to refer to only a singular entity, but include the general class of which a specific example may be used for illustration. The terms "a", "an", and "the" are used interchangeably with the term "at least one". The phrases "at least one of" and "comprises at least one of" followed by a list refers to any one of the items in the list and any combination of two or more items in the list. All numerical ranges are inclusive of their endpoints and non-integral values between the endpoints unless otherwise stated.

The terms "first" and "second" are used in this disclosure. It will be understood that, unless otherwise noted, those terms are used in their relative sense only. For these components, the designation of "first" and "second" may be applied to the components merely as a matter of convenience in the description of one or more of the embodiments.

The terms "multiple" and "a plurality" refer to more than one.

The term "opening" should be understood to be a void space in the mechanical fastener material that is surrounded by the mechanical fastener web. One opening is typically enclosed by two of the multiple strands.

The term "web" can refer to a continuous or running web, sometimes having an indefinite length. A web can typically be handled in a roll-to-roll process. The term "machine direction" (MD) as used above and below denotes the direction of a running web of material during the manufacturing of the mechanical fastener. When a mechanical fastening strip is cut from a continuous web, the machine direction corresponds to the length "L" of the mechanical fastening strip. As used herein, the terms "machine direction" and "longitudinal direction" are typically used interchangeably. The term "cross-machine direction" (CD) as used above and below denotes the direction which is essentially perpendicular to the machine direction. When a mechanical fastening strip is cut from a continuous web, the cross-machine direction corresponds to the width "W" of the mechanical fastening strip.

The above summary of the present disclosure is not intended to describe each disclosed embodiment or every implementation of the present disclosure. The description that follows more particularly exemplifies illustrative embodiments. It is to be understood, therefore, that the drawings and following description are for illustration purposes only and should not be read in a manner that would unduly limit the scope of this disclosure.

BRIEF DESCRIPTION OF THE DRAWINGS

The disclosure may be more completely understood in consideration of the following detailed description of various embodiments of the disclosure in connection with the accompanying drawings, in which.

DETAILED DESCRIPTION

Reference will now be made in detail to embodiments of the disclosure, one or more examples of which are illustrated in the drawings. Features illustrated or described as part of one embodiment can be used with other embodiments to yield still a third embodiment. It is intended that the present disclosure include these and other modifications and variations.

Figure 1A:
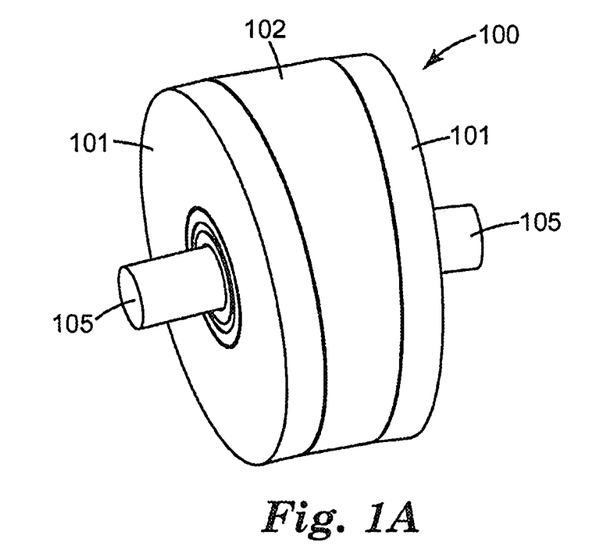
FIG. 1A is a perspective view of one embodiment of diverging disks and a support surface useful for carrying out the method according to the present disclosure.
Figure 1B:
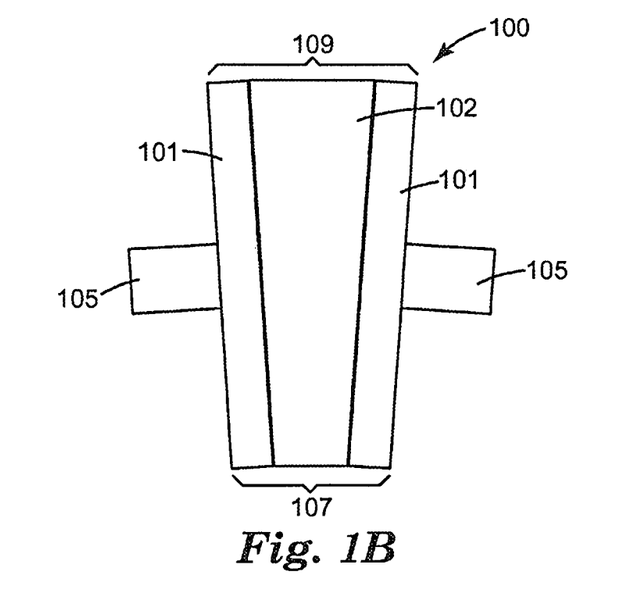
FIG. 1B is a side view of the diverging disks and support surface shown in FIG. 1A.

FIGS. 1A and 1B illustrate two views of an embodiment of diverging disks 101 and a support surface 102 useful for the method of making a mechanical fastener disclosed herein. The two diverging disks 101 are laterally spaced and have the support surface 102 between them. In the illustrated embodiment, the support surface 102 is connected to the two diverging disks 101, and the diverging disks 101 and support surface 102 together form an integral roller 100. Roller 100 can optionally be provided with a shaft 105 extending perpendicular to each diverging disk as shown in FIG. 1B. The shafts 105 may be useful, in some embodiments, for mounting and/or rotating the diverging disks although other mechanisms for mounting and rotating the disks are possible.

Any surface over which a web is bent or wrapped around is believed to impart a force on the web that is normal or perpendicular to the web. In the method disclosed herein, the support surface is believed to impart such a force on the slit web. In FIGS. 1A and 1B, support surface 102 is flush with the peripheral surfaces of the diverging disks 101. The amount of force on part of the slit web may be increased, for example, by changing the geometry of the support surface. In some embodiments, support surface 102 bulges outward beyond the peripheral surfaces of the diverging disks 101. In these embodiments, the support surface may impart a larger force on at least a portion of the slit web. In some of these embodiments, the support surface may be considered a crowned surface, in which the path length for the slit web is highest in the center of the web. The support surface 102 may be flush with the peripheral surfaces of the diverging disks 101 around the entire periphery of the diverging disks as shown in FIGS. 1A and 1B or may bulge outward around the entire periphery of the diverging disks. However, in other embodiments, the support surface may be present only on one side of diverging disks 101. In other words, the support surface may extend to the peripheral surface for only a portion of the diverging disks.

Diverging disks 101 and support surface 102 need not be connected to form a roller 100 as shown in FIGS. 1A and 1B. In some embodiments, the support surface can be separate from the diverging disks 101 and need not rotate with the diverging disks 101. That is, the support surface may be stationary. The support surface can have a portion that extends beyond the diverging disks, for example, in the direction of the incoming slit web path. In these embodiments, the support surface can serve as a guiding surface that aligns and directs the slit web onto the peripheral surfaces of the diverging disks.

The diverging disks 101 and the peripheral surface 102 may be made from the same or different materials. In some embodiments, they both can be made of metal (e.g., aluminum or steel). In some embodiments, the diverging disks 101 can be made from a high-friction material (e.g., a rubbery material), and the support surface 102 can be made from a low-friction material or provided with a low-friction coating. Particularly in embodiments in which the support surface is stationary, it may be useful for the support surface to be made from a low-friction material or coated with a low-friction coating. Suitable low-friction materials include smooth or polished metal (e.g., aluminum or steel), smooth plastic (e.g., polytetrafluoroethylene, polyoxymethylene, polyether ether ketone, or other engineering plastics), or a smooth plastic composite material. Suitable low-friction coatings include a plasma or polytetrafluoroethylene coating. In some embodiments described in further detail below, the support surface is capable of being heated. In these embodiments, the support surface is typically made of metal.

As shown in FIGS. 1A and 1B, diverging disks 101 are positioned such that a portion of their peripheral surfaces have a closer spacing at one location 107 and a larger spacing at a second location 109. When the side edges of a slit web are held to the peripheral surfaces of diverging disks 101, the slit web will spread apart during the rotation of the diverging disks. Various embodiments of the slit web useful in the method disclosed herein before and after they are spread are illustrated in FIGS. 2A through 2C, 3A, 3B, 4A, and 4B and described below.

Figure 2A:
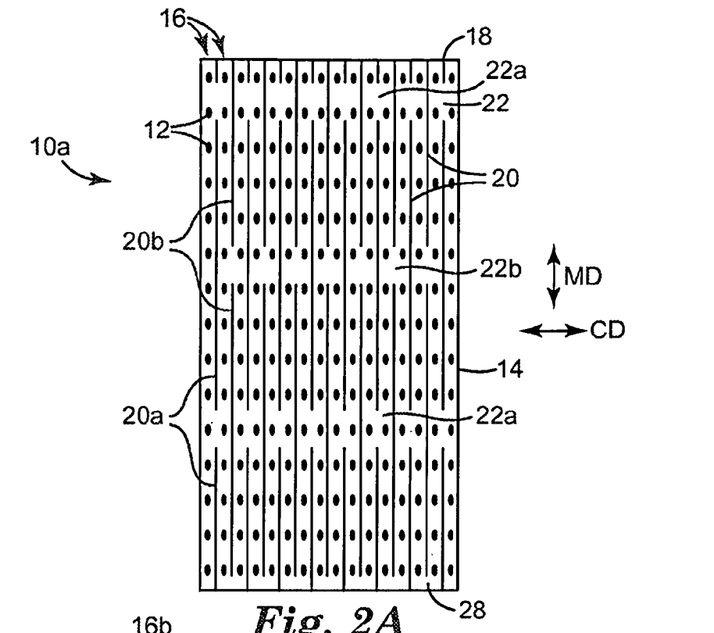
FIG. 2A is a top view of an embodiment of a portion of a slit web useful for the method of making a mechanical fastener disclosed herein.

FIG. 2A illustrates an example of a portion of a slit web 10a with interrupted slits 20 that can be spread using the method disclosed herein. In the illustrated embodiment, the mechanical fastening elements of the slit web 10a are male fastening elements 12. Illustrated slit web 10a has a thermoplastic backing 14 with multiple rows 16 of male fastening elements 12 projecting from a first surface of the backing 14. The first surface of the backing is the surface that is visible in FIG. 2A. The first surface (that is, the surface with mechanical fastening elements) can also be called the first major surface in any of the embodiments disclosed herein. In the illustrated embodiment, the multiple rows 16 of male fastening elements 12 are aligned in the MD although this is not a requirement. The term "row" refers to male fastening elements lined up in a particular direction. The row or line of male fastening elements may be substantially straight.

In the portion of slit web 10a, interrupted slits 20 are cut into the backing between some pairs of adjacent rows 16 of male fastening elements 12. When an interrupted slit is cut between adjacent rows of male fastening elements 12, it typically means that the particular slit does not cross over a row of male fastening elements 12. The illustrated interrupted slits 20 are linear in the same direction as the multiple rows 16, which in the illustrated embodiment is the MD, and extend from the top edge 18 to the bottom edge 28 of the backing 14. The interrupted slits are interrupted by intact bridging regions 22 of the backing 14. The bridging regions 22 are regions where the web is not cut through, and at least a portion of the bridging regions 22 can be considered collinear with interrupted slit 20. The intact bridging regions 22 divide the interrupted slits into a series of spaced apart slit portions 20a. The spaced apart slit portions 20a and 20b and consequently bridging regions 22a and 22b of adjacent interrupted slits are staggered in a direction "CD" perpendicular to the direction "MD" of the interrupted slits 20. The bridging regions are staggered such that bridging region 22b is located substantially midway between bridging regions 22a in the direction "MD". However, in some embodiments, the upstanding posts 12, interrupted slits 20, and bridging regions 22, 22a, and 22b may be positioned in other arrangements. When the slit portions and bridging regions are staggered, the number of bridging regions necessary to make the slit mechanical fastener handle as an integral unit can be minimized.

In some embodiments of the method disclosed herein, the interrupted slits 20 extend in the MD. In some embodiments, the interrupted slits extend in a first direction that is non-parallel to the CD. When it is said that an interrupted slit "extends" in a first direction, it is meant that the slit is arranged or aligned in the first direction or at least predominantly in that direction. The slit may be linear. As used herein a "linear" slit can be defined by two points in a line on the web. The slit may also be substantially linear, which means that the slit can have a slight curvature or slight oscillation. Some oscillation or curvature may result, for example, from the process of slitting a continuous web as would be understood by a person skilled in the art. In some embodiments of mechanical fasteners with male fastening elements made according to the method of the present disclosure, any oscillation or curvature is such that the slit generally does not have a portion that crosses over a row of male fastening elements aligned in the first direction. The interrupted slit may also have a wavy or sawtooth pattern with a small amplitude, and such a slit would also be considered to extend in predominantly in a certain direction.

The particular arrangement of the bridging regions 22, 22a, and 22b can be designed, for example, based on the desired length of the slits and the amount of spreading desired for the multiple strands 26. Various lengths of bridging regions 22, 22a, and 22b may be useful. In some embodiments, any bridging regions 22 in a given interrupted slit 20 have a combined length in the direction of the interrupted slit of up to 50 (in some embodiments, 40, 30, 25, 20, 15, or 10) percent of the length of the slit web in the MD. In some embodiments, for maximizing the ability of the slit web 10a to spread, it may be desirable to minimize the combined length of the bridging regions in the direction of the interrupted slit. Minimizing the combined length of the bridging regions 22 in the direction of the interrupted slit may be accomplished by at least one of minimizing the length of any particular bridging region 22 or maximizing the distance between bridging regions 22. In some embodiments, the length of one bridging region in the direction of the interrupted slit is up to 3, 2, or 1.5 mm and at least 0.25, 0.5, or 0.75 mm. In some embodiments, the number of bridging regions along the length of the slit web 10a in the direction of the interrupted slit is up to 1.5, 1.25, 1.0, 0.75, 0.60, or 0.5 per cm. The distance between bridging regions 22 in the direction of the interrupted slit may be, for example, at least 0.75, 1.0, 1.25, 1.5, or 1.75 cm. Furthermore, the length of the interrupted slit portions between bridging regions can be adjusted and may be selected to maximize the distance between bridging regions. In some embodiments, the length of the slit portions 20a, 20b is at least 8 (in some embodiments, at least 10, 12, 14, 15, 16, 17, 18, 19, or 20) mm. Typically, the interrupted slits of the slit webs 10a useful for practicing the present disclosure have longer slit regions and shorter bridging regions than perforations that are designed to allow easy separation of two parts of a film.

In some embodiments, slit portions 20a, 20b have a regular pattern that repeats down the slit web 10a. In some embodiments, spacing (e.g., in the MD or other direction of the interrupted slits) between slit portions 20a may be uniform or substantially uniform (that is, the spacing may differ by up to 2 percent, 1 percent, or less than 1 or 0.5 percent) although this is not a requirement.

For any of the embodiments of the method of making a mechanical fastener disclosed herein, the number of interrupted slits and resulting openings may be adjusted depending on the desired spread mechanical fastening web. The interrupted slits may be evenly spaced or unevenly spaced as desired. In some embodiments, there are up to 10, 9, 8, 7, 6, 5, 4, 3, 2, or 1 interrupted slits per 10 mm across the width of the slit web in the CD. Changing the number of interrupted slits across the slit web may be related to the number of rows of male fastening elements between any two adjacent interrupted slits, depending on the density of the male fastening elements on the backing. The number of rows of male fastening elements between any two adjacent interrupted slits may be adjusted depending on the requirements of the application. In some embodiments, there are up to 10, 9, 8, 7, 6, 5, 4, 3, 2 rows, or 1 row of male fastening elements between any two adjacent interrupted slits. Typically, the width dimension of each of the multiple strands formed between interrupted slits is wider than at least the bases of the upstanding posts of the male fastening elements. In some embodiments, there is an interrupted slit between every row or every other row of male fastening elements. In the illustrated embodiment, the interrupted slits 20 are evenly spaced among the rows of male fastening elements 12 although this is not a requirement. For multiple rows 16 of male fastening elements 12 that are evenly spaced, as illustrated, the spacing (e.g., distance in the CD in the illustrated embodiment) between multiple rows 16 may differ by up to 10, 5, 2.5, or 1 percent. Likewise, for interrupted slits that are evenly spaced, the spacing (e.g., distance in the CD) between the interrupted slits may differ by up to 10, 5, 2.5, or 1 percent.

Figure 2B:
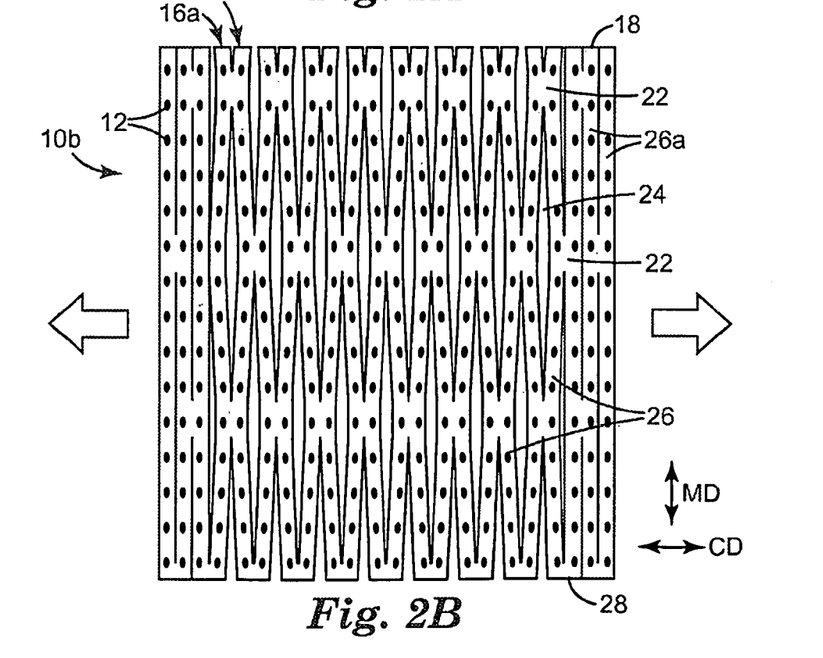
FIG. 2B is a top view of the portion of the slit web similar to FIG. 2A after it is spread according to the method disclosed herein.
Figure 2C:
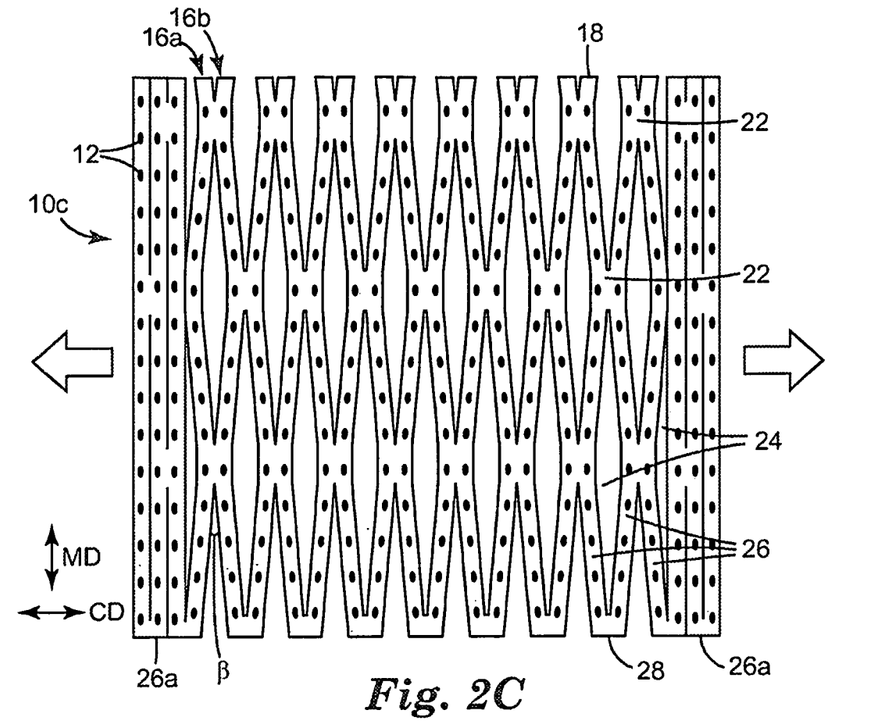
FIG. 2C is a top view of the portion of the slit web of FIG. 2B after it is spread to a greater extent than shown in FIG. 2B.

FIGS. 2B and 2C illustrate the effect of spreading the slit backing like that shown in FIG. 2A to different extents. When the slit backing 10b is spread in the direction of the arrows shown, multiple strands 26 of the backing are provided, and the separation between at least some of the multiple strands creates openings 24. The method according to the present disclosure typically increases the width of the slit web (that is, the dimension in the CD).

FIG. 2C illustrates a greater amount of spreading than FIG. 2B. The amount of spreading provided in the method disclosed herein can be controlled by a variety of factors including the geometry of the diverging disks and the support surface, and the amount of tension in the machine direction. In some embodiments, spreading the slit web is carried out with multiple sets of diverging disks in a series, which can also affect the extent of spreading. In some embodiments, the width of the spread mechanical fastening web is at least 5, 10, 15, 20, or 25 percent greater than the width of the input slit web. In some embodiments, the width of the spread mechanical fastening web is up to 40, 50, 75, 100, 150, or 200 percent greater than the width of the input slit web.

In the embodiment illustrated in FIG. 2C, at least two strands 26a, including at least two rows of male fastening elements on each edge of the mechanical fastener, are not separated. The portion of the edges of the slit web that are held to the peripheral surfaces of the diverging disks are typically not spread apart. A spread mechanical fastening web having strands on the edge that are not spread apart may be advantageous in some embodiments, for example, to provide a reticulated mechanical fastening strip or patch with a straight edge.

While FIGS. 2A through 2C illustrate a backing 14 with male fastening elements 12 that comprise upstanding posts, it should be understood that a loop material can be slit to provide slit web 10a and spread using the method disclosed herein in the same manner to the same extent as spread mechanical fastening webs 10b and 10c.

Figure 3A:
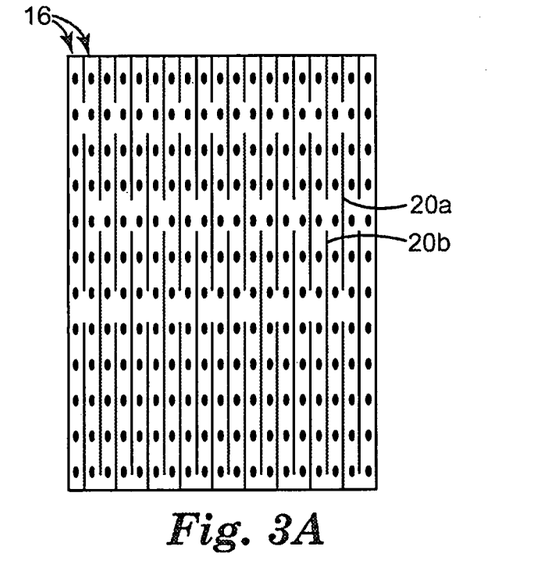
FIG. 3A is a top view of another embodiment of a portion of a slit web useful for the methods of making a mechanical fastener disclosed herein.
Figure 3B:
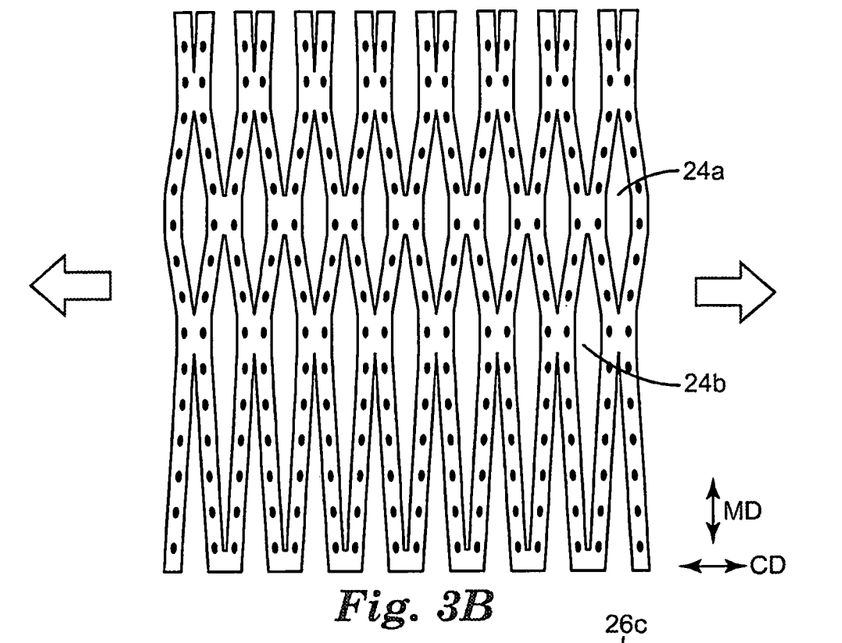
FIG. 3B is a top view of a portion of the slit web similar to FIG. 3A after it is spread according to the method disclosed herein.

FIG. 3A illustrates an example of a slit web portion having male fastening elements, which is similar to the portion of slit web 10a shown in FIG. 2A. However, in the embodiment shown in FIG. 3A, slit portions 20a have different lengths than slit portions 20b of adjacent slits, which results in openings 24a and 24b having different sizes after the slit web is spread as shown in FIG. 3B. That is, openings 24a are shorter in the MD than openings 24b. The slit portions of the smaller size 20a and slit portions of the larger size 20b each may be aligned with each other across the slit web as shown in FIG. 3A. Or in other embodiments, slits of the same size may be offset relative to each other in a regular pattern. Furthermore, referring again to FIG. 2A, the length of the bridging regions 22 may be made to vary within a strand 26 or between strands 26 as desired for a particular application or appearance. Although FIGS. 3A and 3B illustrate mechanical fasteners with male fastening elements, the same slitting pattern and spreading using the method disclosed herein can be carried out with a loop material.

Figure 4A:
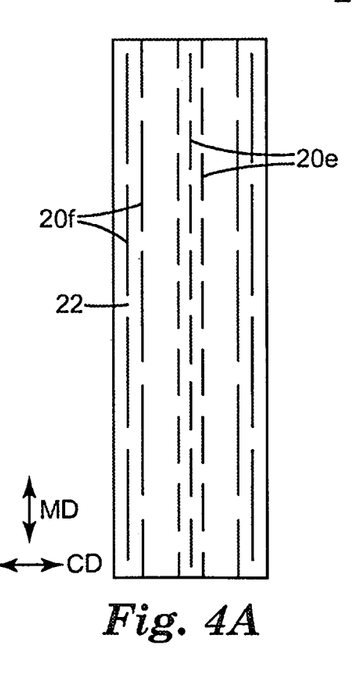
FIG. 4A is a schematic top view of another embodiment of a portion of a slit web useful for the methods of making a mechanical fastener disclosed herein.
Figure 4B:
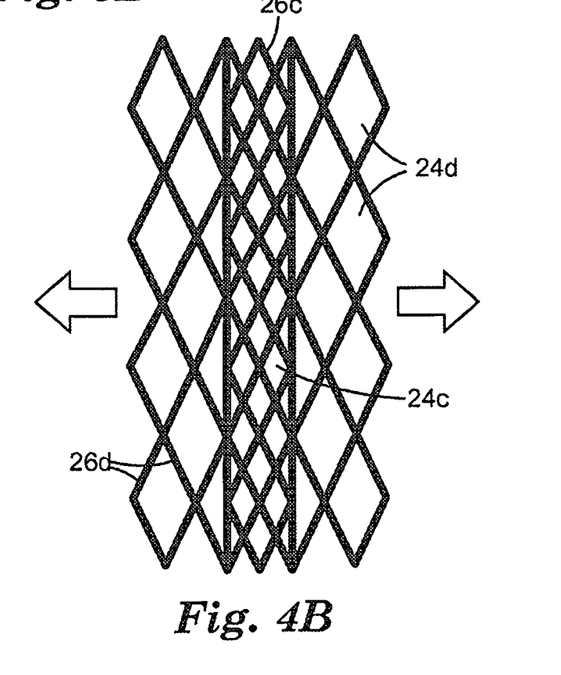
FIG. 4B is a schematic top view of the portion of the slit web of FIG. 4A after it is spread according to the method disclosed herein.

FIG. 4A illustrates an example of a slit web having mechanical fastening elements, which is similar to the slit mechanical fastener 10a shown in FIG. 2A. However, in the embodiment shown in FIG. 4A, slit portions 20e have different lengths than slit portions 20f, which results in openings 24c and 24d having different sizes after the slit web is spread as shown in FIG. 4B. In contrast to the embodiment shown in FIGS. 3A and 3B, which illustrates interrupted slits with slit portions of different lengths in the MD and the corresponding resulting openings, FIGS. 4A and 4B illustrate patterns of slit portions of different lengths in different zones in the CD of the slit web. The multiple strands 26c and 26d have a different appearance from each other in the same spread mechanical fastening web, for example, multiple strands 26c and 26b zig-zag or undulate with a different wavelength and amplitude. The slit web and the spread mechanical fastening web shown in FIGS. 4A and 4B, respectively, may include male or female mechanical fastening elements (not shown).

For any of the embodiments of the method of making a mechanical fastener disclosed herein, the openings formed by the separation of the multiple strands between at least some of the bridging regions are in the form of a repeating pattern of geometric shapes. In the illustrated embodiments, the geometric shapes are polygons, which may be quadrilaterals such as rhombuses. In some embodiments of the spread mechanical fastening web, including the embodiment illustrated in FIG. 2C, the multiple strands of the web attached to each other at least at some of the intact bridging regions form an angle β of less than 90 degrees, in some embodiments, less than 60 degrees, 45 degrees, or 20 degrees, and in some embodiments, in a range from 0.5 to 20 degrees. For example, in some embodiments, when a slit web having 19 mm slit portions 20a is spread so that the width of the spread mechanical fastening web is 100% greater than the input slit web, the angle β is typically in a range from about 5 to 10 degrees. In some embodiments, curved lines may be used, which can result in crescent shaped openings after spreading. As shown in FIG. 4B, there may be more than one repeating pattern of geometric shaped openings. The openings may be evenly spaced or unevenly spaced as desired. For openings that are evenly spaced, the spacing (e.g., distance in the CD) between the openings may differ by up to 10, 5, 2.5, or 1 percent.

Although the methods of making mechanical fastener illustrated in FIGS. 2A through 2C, 3A and 3B, and 4A and 4B each show interrupted slits extending parallel to the MD of the slit web, interrupted slits may be made in any desired direction not parallel to the CD. For example, interrupted slits may be made at an angle from 1 to 85 degrees to the MD of the slit web. In some embodiments, interrupted slits are made at an angle in a range from 35 to 55 degrees (e.g., 45 degrees) to the MD of the slit web.

The method according to the present disclosure may be useful for any width of the slit web in the CD. For example, the slit web may have a width in the CD in a range from 1 cm to 10 cm, 1 cm to 5 cm, or 1 cm to 3 cm wide.

In some embodiments, the slit web useful in the method disclosed herein or the resulting spread mechanical fastening web are made of a thermoplastic material. Suitable thermoplastic materials for mechanical fasteners include polyolefin homopolymers such as polyethylene and polypropylene, copolymers of ethylene, propylene and/or butylene; copolymers containing ethylene such as ethylene vinyl acetate and ethylene acrylic acid; polyesters such as poly(ethylene terephthalate), polyethylene butyrate and polyethylene napthalate; polyamides such as poly(hexamethylene adipamide); polyurethanes; polycarbonates; poly(vinyl alcohol); ketones such as polyetheretherketone; polyphenylene sulfide; and mixtures thereof. Typically, the thermoplastic is a polyolefin (e.g., polyethylene, polypropylene, polybutylene, ethylene copolymers, propylene copolymers, butylene copolymers, and copolymers and blends of these materials).

In the embodiments of the slit web useful in the method disclosed herein or the resulting spread mechanical fastening web that includes male fastening elements, the backing and the male fastening elements are typically integral (that is, formed at the same time as a unit, unitary). Upstanding posts on a backing can be made, for example, by feeding a thermoplastic material onto a continuously moving mold surface with cavities having the inverse shape of the posts. The thermoplastic material can be passed between a nip formed by two rolls or a nip between a die face and roll surface, with at least one of the rolls having the cavities. The cavities may be in the inverse shape of a capped post having a loop-engaging head or may be in the inverse shape of an upstanding post without loop-engaging heads (e.g., a precursor to a male fastening element). Pressure provided by the nip forces the resin into the cavities. In some embodiments, a vacuum can be used to evacuate the cavities for easier filling of the cavities. The nip typically has a large enough gap such that a coherent backing is formed over the cavities. The mold surface and cavities can optionally be air or water cooled before stripping the integrally formed backing and upstanding hook elements from the mold surface such as by a stripper roll. If the posts formed upon exiting the cavities do not have loop-engaging heads, loop-engaging heads could be subsequently formed into hooks by a capping method as described in U.S. Pat. No. 5,077,870 (Melbye et al.). Typically, the capping method includes deforming the tip portions of the hook elements using heat and/or pressure. The heat and pressure, if both are used, could be applied sequentially or simultaneously.

Suitable tool rolls include those formed from a series of plates defining a plurality of post-forming cavities about its periphery such as those described, for example, in U.S. Pat. No. 4,775,310 (Fischer). Cavities may be formed in the plates by drilling or photoresist technology, for example. Other suitable tool rolls may include wire-wrapped rolls, which are disclosed along with their method of manufacturing, for example, in U.S. Pat. No. 6,190,594 (Gorman et al.). Another example of a method for forming a thermoplastic backing with upstanding posts includes using a flexible mold belt defining an array of upstanding post-shaped cavities as described in U.S. Pat. No. 7,214,334 (Jens et al.). Yet other useful methods for forming a thermoplastic backing with upstanding posts can be found in U.S. Pat. No. 6,287,665 (Hammer), U.S. Pat. No. 7,198,743 (Tuma), and U.S. Pat. No. 6,627,133 (Tuma).

The male fastening elements in the slit web or spread mechanical fastening web disclosed herein may have loop-engaging heads that have an overhang or may be upstanding posts having distal tips that can be formed into loop-engaging heads, if desired. The term "loop-engaging" as used herein relates to the ability of a male fastening element to be mechanically attached to a loop material. Generally, male fastening elements with loop-engaging heads have a head shape that is different from the shape of the post. For example, the male fastening element may be in the shape of a mushroom (e.g., with a circular or oval head enlarged with respect to the stem), a hook, a palm-tree, a nail, a T, or a J. The loop-engageability of male fastening elements may be determined and defined by using standard woven, nonwoven, or knit materials. A region of male fastening elements with loop-engaging heads generally will provide, in combination with a loop material, at least one of a higher peel strength, higher dynamic shear strength, or higher dynamic friction than a region of posts without loop-engaging heads. Male fastening elements that have "loop-engaging overhangs" or "loop-engaging heads" do not include ribs that are precursors to fastening elements (e.g., elongate ribs that are profile extruded and subsequently cut to form male fastening elements upon stretching in the direction of the ribs). Such ribs would not be able to engage loops before they are cut and stretched. Such ribs would also not be considered upstanding posts. Typically, male fastening elements that have loop-engaging heads have a maximum thickness dimension (in either dimension normal to the height) of up to about 1 (in some embodiments, 0.9, 0.8, 0.7, 0.6, 0.5, or 0.45) millimeter. In some embodiments, the male fastening elements have a maximum height (above the backing) of up to 3 mm, 1.5 mm, 1 mm, or 0.5 mm and, in some embodiments a minimum height of at least 0.05 mm, 0.1 mm, or 0.2 mm. In some embodiments, the upstanding posts have aspect ratio (that is, a ratio of height to width at the widest point) of at least about 2:1, 3:1, or 4:1.

In some embodiments of a slit web having male fastening elements useful for practicing the present disclosure, at least a portion of each loop-engaging overhang (e.g., at the cap or head) extends at a nonzero angle to the direction of the interrupted slits. In some embodiments, each male fastening element has a cap with loop engaging overhangs extending in multiple (i.e., at least two) directions. For example, the upstanding post may be in the shape of a mushroom, a nail, a palm tree, or a T. In some embodiments, the upstanding posts are provided with a mushroom head (e.g., with an oval or round cap distal from the thermoplastic backing). In other embodiments, loop-engaging overhangs (e.g., at the cap or head) on the upstanding posts of the slit web extend parallel to the MD. For example, the upstanding posts may have the shape of a J (e.g., as shown in U.S. Pat. No. 5,953,797 (Provost et al.).

In spread mechanical fastening web 10b and 10c illustrated in FIGS. 2B and 2C, the male fastening elements 12 on a first strand 26 are arranged in a series 16a that is non-parallel to a series 16b of male fastening elements 12 on a second, adjacent strand 26. The series 16a and 16b of multiple upstanding posts and the multiple strands themselves from which they project can undulate or zig-zag along the length of the spread mechanical fastening web 10b or 10c, for example, from the top edge 18 to the bottom edge 28. In the illustrated embodiment, the caps visible on the upstanding posts of the male fastening elements 12 have an oval shape, and these caps are oriented in different directions along the multiple strands 26 in the MD. When the caps are circular in shape, it may not be observed that the caps are oriented in different directions along the multiple strands 26, unless the cap is marked in some way. In the illustrated embodiment, the caps on a first strand 26 are oriented in a different direction than the caps on a second, adjacent strand 26. In embodiments in which slit web 10a includes male fastening elements having loop-engaging overhangs aligned only parallel to the MD, spreading the slit web 10a typically results in the loop-engaging overhangs oriented in different directions along the multiple strands in the MD as shown in FIG. 2C. When loop-engaging overhangs are oriented in multiple directions (e.g., not only one direction such as the machine direction), enhanced engagement of a loop material may advantageously result.

Loop materials useful for practicing some embodiments of the present disclosure (e.g., when the mechanical fastener is a loop material) can be any suitable material that interlocks with corresponding hook fastening elements. In some embodiments, the loop fastening elements are typically formed from knitted fabrics, woven fabrics, or non-woven fabrics. The term "non-woven" refers to a material having a structure of individual fibers or threads that are interlaid but not in an identifiable manner such as in a knitted fabric. Examples of non-woven webs include spunbond webs, spunlaced webs, airlaid webs, meltblown web, and bonded carded webs. The spread mechanical fastening web prepared by the method disclosed herein may include fiber loops projecting from a knitted, woven, or non-woven backing or may be extrusion-bonded, adhesive-bonded, and/or sonically-bonded fiber loops. Useful loop materials may be made of natural fibers (e.g., wood or cotton fibers), synthetic fibers (e.g., thermoplastic fibers), or a combination of natural and synthetic fibers. Examples of suitable materials for forming thermoplastic fibers include polyolefins (e.g., polyethylene, polypropylene, polybutylene, ethylene copolymers, propylene copolymers, butylene copolymers, and copolymers and blends of these polymers), polyesters, and polyamides. The fibers may also be multi-component fibers, for example, having a core of one thermoplastic material and a sheath of another thermoplastic material.

In some embodiments, the loop material comprises a fibrous layer disposed on a backing. Suitable backings include textiles, paper, thermoplastic films (e.g., single- or multilayered films, coextruded films, laterally laminated films, or films comprising foam layers), and combinations thereof. For thermoplastic backings, the thermoplastic can be any of those described above in connection with a thermoplastic backing having male fastening elements. Examples of suitable loop materials are described, for example, in U.S. Pat. No. 5,256,231 (Gorman et al.) and U.S. Pat. No. 5,389,416 (Mody et al.). As described in U.S. Pat. No. 5,256,231 (Gorman et al), the fibrous layer in a loop material according to some embodiments disclosed herein comprises arcuate portions projecting in the same direction from spaced anchor portions on the backing.

In embodiments wherein the mechanical fastening web either has male fastening elements (e.g., upstanding posts) or a fibrous layer on a backing, the thickness of the backing may be up to about 400, 250, 150, 100, 75 or 50 micrometers, depending on the desired application. In some embodiments, the thickness of the backing is in a range from 30 to about 225 micrometers, from about 50 to about 200 micrometers, or from about 100 to about 150 micrometers. In some embodiments wherein the backing is a thermoplastic backing, the thermoplastic backing has stretch-induced molecular orientation, for example, when the thermoplastic backing is stretched after formation of upstanding posts. In other embodiments, the thermoplastic backing or the spread mechanical fastening web is not provided with macroscopic stretch-induced molecular orientation in the direction of the interrupted slits or in the direction of spreading. In these embodiments, there may be some stress-induced orientation localized in the bridging regions.

Figure 5A:
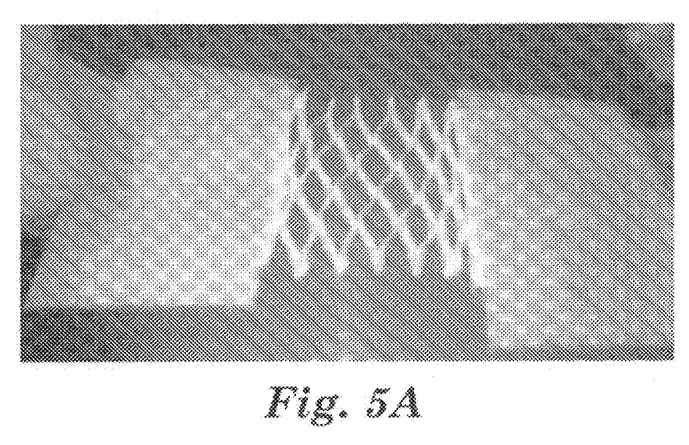
FIG. 5A is a photograph illustrating twisting of strands of a slit web portion when it is spread apart.
Figure 5B:
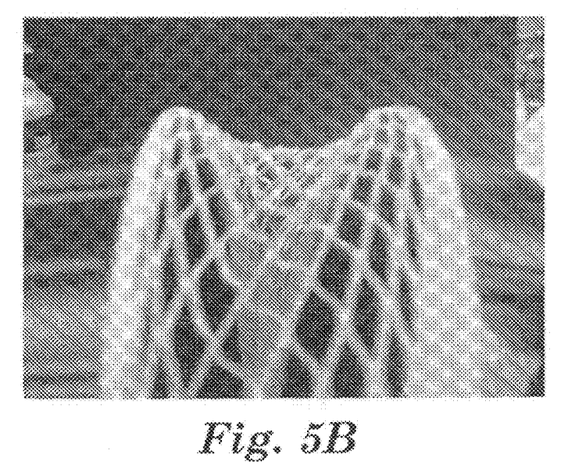
FIG. 5B is a photograph illustrating the spreading of a slit web using diverging disks without a support surface.

The support surface useful in the method of the present disclosure can advantageously allow spreading of the slit web without allowing all of the multiple strands of the spread mechanical fastening web to twist out-of-plane and without allowing the center of the spread mechanical fastening web to drop to a lower plane. Twisting out-of-plane can result when spreading a slit web as shown in the photograph of FIG. 5A. Pieces of loop material were attached to the edges of a slit mechanical fastener web portion with male fastening elements such as that shown in FIG. 2A. When the pieces of loop material were pulled apart, the individual strands of the slit web tended to twist out of the plane of the web as shown in FIG. 5A. The amount of out-of-plane twisting is typically affected, for example, by the extent to which the slit backing is spread. Also, elongating a material in the CD typically causes the material to contract in the MD. If the slit web useful in the method disclosed herein is spread on diverging disks without a support surface, the tendency to contract in the MD will prompt the center of the web to drop to a smaller radius path as shown in FIG. 5B. At the same time, the strands of the spread mechanical fastening web tend to twist out-of-plane as described above. Twisted strands of the spread mechanical fastening web create a non-uniform contact surface, which can complicate heat transfer to the web and complicate the use of a nip in further web processing (e.g., annealing or laminating as described, below) since the twisted strands may be crushed by the nip.

When the edges of the slit web are held to the peripheral surfaces of the diverging disks, the tendency of the slit web to contract in the MD results in internal tension in the spread mechanical fastening web. The support surface useful in the method of the present disclosure in combination with this internal tension constrains the spread mechanical fastening web to a larger radius path, pulls the strands of the spread web flat, and prevents them from twisting. As a result, the spread mechanical fastening web strands typically have more uniform contact area for heat transfer and are more easily tolerated in later web processes. Accordingly, in some embodiments, the method disclosed herein may be considered to maintain or constrain at least some of the multiple strands in a substantially coplanar arrangement. A substantially "coplanar" arrangement refers to the strands occupying substantially the same plane. The term "substantially" in this regard can mean that at least some of the multiple strands can be twisted out of plane by up to 15, 10, or 5 degrees. The phrase "at least some" with regard to the multiple strands being constrained refers to at least 25, 50, 75, or 90 percent or more of the multiple strands being constrained. In some embodiments, all of the strands may be in a coplanar arrangement on the support surface and diverging disks.

A number of web handling or web processing techniques may be useful in a variety of combinations for some embodiments of the method disclosed herein. For any of the aforementioned embodiments of the method according to the present disclosure, providing a slit web having upstanding posts or loops with interrupted slits can be carried out in a variety of ways. For example, rotary die cutting of a continuous web having male fastening elements or loops as described above may be useful. Interrupted slits can be made, for example, by using rotary cutting blades having gaps to form the bridging regions. The height of the blade in the gaps may be adjusted to allow for the bridging regions to be partially cut or not cut at all, depending on the desired embodiment. Other cutting methods (e.g., laser cutting) may also be useful. Cutting can be performed from either surface of the continuous web. A slit may be cut "through" the web having mechanical fastening elements, which means that the slit cuts through the entire thickness of the web. In other embodiments, the slit may be a partial-depth slit as long as the diverging disks can pull apart the partial depth slit. The partial-depth slit may penetrate, for example, 80, 85, or 90 percent of the thickness of the web or more, which means the solution to the equation:

(depth of the slit divided by the thickness of the web)×100 is at least 80, 85, or 90 in some embodiments. Other methods of slitting a web can be found, for example, in U.S. Pat. Appl. Pub. No. 2011/0313389 (Wood et al.).

When male fastening elements are formed as described above, for example, where a thermoplastic material is fed onto a continuously moving mold surface with cavities having the inverse shape of upstanding posts, slitting the web and spreading the slit web according to the method disclosed herein can be carried out before or after a capping step is carried out to form loop-engaging heads. Also, deforming the distal tip to form a cap can be carried out, for example, after slitting through the web but before spreading the slit web; after spreading the slit web but before annealing (described below); or after annealing as desired. The formation of male fastening elements can also include a step in which the shape of the cap is changed, for example, as described in U.S. Pat. No. 6,132,660 (Kampfer). Such a cap modifying step can be carried out directly after capping or after any of the slitting, spreading, or further processing steps described herein.

In some embodiments, the method according to the present disclosure further comprises heating the spread mechanical fastening web. In some embodiments, the method according to the present disclosure further comprises annealing the spread mechanical fastening web. In some embodiments, annealing comprises heating the spread mechanical fastening web. In some embodiments, annealing comprises heating and then cooling (e.g., rapidly cooling) the spread mechanical fastening web to maintain its configuration. Heating and/or annealing can be carried out, for example, after the spread mechanical fastening web has been spread to the final desired extent or at an intermediate stage, for example, if the spread mechanical fastening web is spread a second time with a second set of diverging disks. Annealing the spread mechanical fastening web can be useful, for example, depending on the extent of spreading, and can be useful to maintain the openings between multiple strands, for example, when the width of the slit web has been increased by at least 50 percent. Annealing can also be useful, for example, for maintaining at least some of the multiple strands in a substantially coplanar arrangement. In some embodiments, heating is only applied to the second surface of the spread mechanical fastening web (i.e., the surface opposite the first surface from which the mechanical fastening elements project) to minimize any damage to the mechanical fastening elements that may result from heating. In some embodiments, the support surface is heated. In these embodiments, the slit web is arranged so that the mechanical fastening elements face away from the support surface. Heating may also be carried out on a continuous web, for example, using heated rollers, for example, after the slit web is spread. Non-contact heating methods such as IR irradiation, hot air treatment, or by directing the web through a heated chamber may also be useful, for example, when the slit web is arranged so that the mechanical fastening elements face toward the support surface.

It may also be useful, in some embodiments, to heat the slit web before it is spread using the diverging disks and support surface using any of the heating methods described above.

Figure 6:
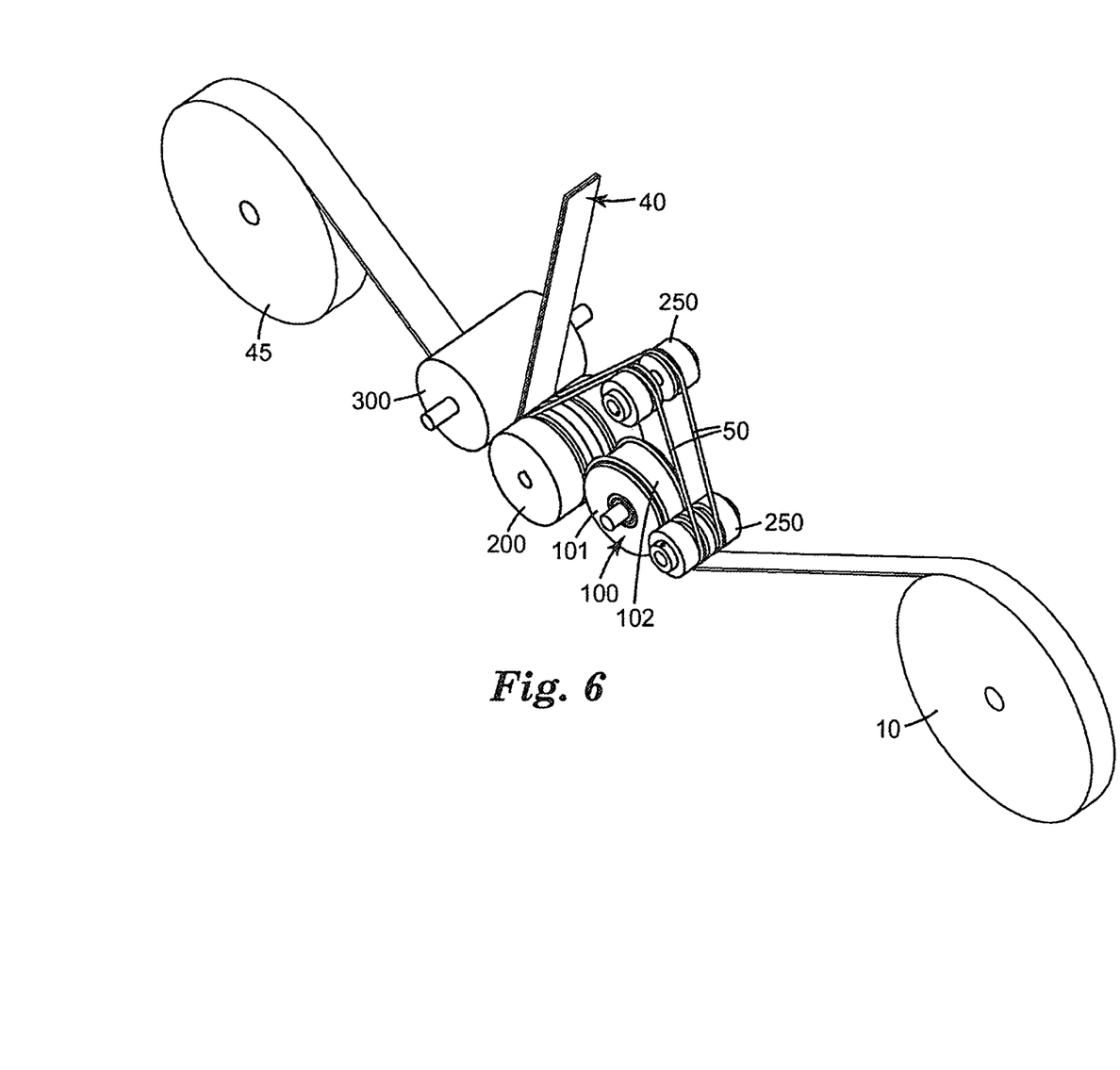
FIG. 6 is a perspective view of an embodiment of an apparatus useful for carrying out the method of making a mechanical fastener disclosed herein.

A perspective view of an embodiment of an apparatus for carrying out the method of the present disclosure is shown in FIG. 6. In FIG. 6, slit web 10 provided on a roll is directed over roller 100. The side edges of slit web 10 are directed over diverging disks 101 to spread the slit web as the diverging disks 101 and the support surface 102 rotate. The side edges of the slit web 10 are held to the diverging disks' peripheral surfaces using belts 50. The paths of the belts 50 around the peripheral surfaces of the diverging disks 101 are determined by rollers 200 and 250. The support surface 102 of roller 100 or roller 200 may optionally be heated to anneal the spread mechanical fastening web after spreading. The support surface 102 may be heated by cartridge heaters and a thermocouple sensor (not shown) to anneal the spread mechanical fastening web immediately upon spreading. The temperature of the support surface can be selected, for example, based on the line speed and the web material such that enough heat energy is transferred to the web but not enough heat energy is provided to melt the mechanical fastening elements. In other embodiments, the support surface of roller 100 may be heated, and roller 200 may be chilled to rapidly cool the annealed web. In the illustrated embodiment, the spread mechanical fastening web is then laminated to a carrier web 45 provided on a roll to form a laminate 40. Lamination is carried out in a nip formed by rollers 200 and 300.

The spread mechanical fastening web can optionally be handled by one or more other rollers. For example, if the spread mechanical fastening web is not laminated directly after being spread by roller 100, it may be directed onto a high-friction roller (e.g., comprising a rubbery material or material with a rough surface). The high-friction roller may be heated or chilled, if desired, or may be useful at room temperature. A high-friction roller may be useful, for example, for holding the spread mechanical fastening web in a spread configuration whether or not the web is annealed. In some embodiments, the spread mechanical fastening web can be directed onto another roller, which may be a rotating heated cylinder (or heated roller) as described above, for annealing in a separate station optionally before laminating the spread mechanical fastening web. In some embodiments, including embodiments in which the support surface is heated to anneal the spread mechanical fastening web, the spread mechanical fastening web is directed onto a rotating chilled cylinder, which further may be provided with forced air nozzles to increase the rate of heat dissipation. In some embodiments, the spread mechanical fastening web is directed over a second set of two rotating diverging disks, wherein in the second set, the two rotating diverging disks are laterally spaced and have a support surface between them as in roller 100 to undergo spreading a second time.

Various methods may be useful for holding the side edges of the slit web 10 to the peripheral surfaces of the diverging disks 101. In the embodiment illustrated in FIG. 6, the side edges of the slit web 10 are held to the peripheral surfaces of the diverging disks 101 using belts 50. In other embodiments, the side edges of the slit web 10 are held to the peripheral surfaces of the diverging disks 101 using pins, vacuum, or forced air jets. Any combination of these methods may also be useful.

In some embodiments, the slit web is coated with adhesive on its surface opposite the mechanical fastening elements. In these embodiments, the slit web is arranged so that the mechanical fastening elements face toward the support surface, and the adhesive coating faces away from the support surface. In these embodiments, the support surface is not heated, but the non-contact heating methods described above may be useful. The spread mechanical fastening web could then come in contact with a chilled cylinder as described above before it is laminated to a carrier.

For any of the embodiments of the method of making a mechanical fastener disclosed herein, the spread mechanical fastening web may be in the form of a roll. The bridging regions interrupting the interrupted slits allow the spread mechanical fastening web to be handled as an integral unit, for example, to be handled in roll form and converted as desired. Although the bridging regions in the spread mechanical fastening web allow it to be handled as an integral unit, it may be useful to laminate the spread mechanical fastening web to a carrier (e.g., even a sacrificial carrier) for ease of handling, for fixing the multiple strands of the spread mechanical fastening web in a spread configuration to maintain the separation between the multiple strands, or for making a fastening laminate for a selected application. The spread mechanical fastening web may be joined to a carrier, for example, by lamination (e.g., extrusion lamination), adhesives (e.g., pressure sensitive adhesives), or other bonding methods (e.g., ultrasonic bonding, compression bonding, or surface bonding).

The carrier 45 may be continuous (i.e., without any through-penetrating holes) or discontinuous (e.g. comprising through-penetrating perforations or pores). The carrier may comprise a variety of suitable materials including woven webs, non-woven webs (e.g., spunbond webs, spunlaced webs, airlaid webs, meltblown web, and bonded carded webs), textiles, plastic films (e.g., single- or multi-layered films, coextruded films, laterally laminated films, or films comprising foam layers), and combinations thereof. In some embodiments, the carrier is a fibrous material (e.g., a woven, nonwoven, or knit material). In some embodiments, the carrier comprises multiple layers of nonwoven materials with, for example, at least one layer of a meltblown nonwoven and at least one layer of a spunbonded nonwoven, or any other suitable combination of nonwoven materials. For example, the carrier may be a spunbond-meltbond-spunbond, spunbond-spunbond, or spunbond-spunbond-spunbond multilayer material. Or, the carrier may be a composite web comprising a nonwoven layer and a dense film layer. Fibrous materials that may provide useful carriers may be made from any of the fibers described above as useful for making loop materials. Useful carriers may have any suitable basis weight or thickness that is desired for a particular application. For a fibrous carrier, the basis weight may range, e.g., from at least about 5, 8, 10, 20, 30, or 40 grams per square meter, up to about 400, 200, or 100 grams per square meter. The carrier may be up to about 5 mm, about 2 mm, or about 1 mm in thickness and/or at least about 0.1, about 0.2, or about 0.5 mm in thickness.

In some embodiments where the spread mechanical fastening web includes a thermoplastic backing (e.g., with upstanding posts or a fibrous layer thereon) the thermoplastic backing can be joined to a fibrous web carrier using surface bonding or loft-retaining bonding techniques. The term "surface-bonded" when referring to the bonding of fibrous materials means that parts of fiber surfaces of at least portions of fibers are melt-bonded to the second surface of the backing, in such a manner as to substantially preserve the original (pre-bonded) shape of the second surface of the backing, and to substantially preserve at least some portions of the second surface of the backing in an exposed condition, in the surface-bonded area. Quantitatively, surface-bonded fibers may be distinguished from embedded fibers in that at least about 65% of the surface area of the surface-bonded fiber is visible above the second surface of the backing in the bonded portion of the fiber. Inspection from more than one angle may be necessary to visualize the entirety of the surface area of the fiber. The term "loft-retaining bond" when referring to the bonding of fibrous materials means a bonded fibrous material comprises a loft that is at least 80% of the loft exhibited by the material prior to, or in the absence of, the bonding process. The loft of a fibrous material as used herein is the ratio of the total volume occupied by the web (including fibers as well as interstitial spaces of the material that are not occupied by fibers) to the volume occupied by the material of the fibers alone. If only a portion of a fibrous web has the second surface of the backing bonded thereto, the retained loft can be easily ascertained by comparing the loft of the fibrous web in the bonded area to that of the web in an unbonded area. It may be convenient in some circumstances to compare the loft of the bonded web to that of a sample of the same web before being bonded, for example, if the entirety of fibrous web has the second surface of the backing bonded thereto. In some of these embodiments, the joining comprises impinging heated gaseous fluid (e.g., ambient air, dehumidified air, nitrogen, an inert gas, or other gas mixture) onto a first surface of the fibrous web carrier while it is moving; impinging heated fluid onto the second surface of the backing while the continuous web is moving, wherein the second surface is opposite the fibrous layer, loop, or upstanding posts the backing; and contacting the first surface of the fibrous web with the second surface of the backing so that the first surface of the fibrous web is melt-bonded (e.g., surface-bonded or bonded with a loft-retaining bond) to the second surface of the backing. Impinging heated gaseous fluid onto the first surface of the fibrous web and impinging heated gaseous fluid on the second surface of the backing may be carried out sequentially or simultaneously. Further methods and apparatus for joining a continuous web to a fibrous carrier web using heated gaseous fluid may be found in U.S. Pat. Appl. Pub. Nos. 2011/0151171 (Biegler et al.) and 2011/0147475 (Biegler et al.).

In some embodiments wherein the spread mechanical fastening web is joined to a carrier, one or more zones of the carrier may comprise one or more elastically extensible materials extending in at least one direction when a force is applied and returning to approximately their original dimension after the force is removed. However, in some embodiments, at least the portion of the carrier joined to the multiple strands of the backing or loop material is not stretchable. In some embodiments, the portion of carrier joined to the multiple strands will have up to a 10 (in some embodiments, up to 9, 8, 7, 6, or 5) percent elongation in the CD. In some embodiments, the carrier may be extensible but nonelastic. In other words, the carrier may have an elongation of at least 5, 10, 15, 20, 25, 30, 40, or 50 percent but substantially no recovery from the elongation (e.g., up to 10 or 5 percent recovery). Suitable extensible carriers may include nonwovens (e.g., spunbond, spunbond meltblown spunbond, or carded nonwovens). In some embodiments, the nonwoven may be a high elongation carded nonwoven (e.g., HEC). In some embodiments, the carrier is not pleated.

In some embodiments wherein the spread mechanical fastening web is joined to a carrier, the carrier is provided with a layer of adhesive. In some of these embodiments, the spread mechanical fastening web is bonded to the carrier with the adhesive to form a laminate, and the adhesive is exposed between the multiple strands in the laminate.

In some embodiments, the method according to the present disclosure includes cutting the spread mechanical fastening web in the CD to provide a spread mechanical fastening patch. Such cutting can be carried out, for example, after the spread mechanical fastening web is laminated to a carrier, and the patch can be considered a fastening laminate.

The fastening laminates made by the methods disclosed herein are useful, for example, in absorbent articles. Absorbent articles may have at least a front waist region, a rear waist region, and a longitudinal center line bisecting the front waist region and the rear waist region, wherein at least one of the front waist region or the rear waist region comprises the fastening laminate disclosed herein. The fastening laminate may be in the form of a fastening tab or landing zone that is bonded to at least one of the front waist region or the rear waist region. A fastening tab may extend outwardly from at least one of the left longitudinal edge or the right longitudinal edge of the absorbent article. In other embodiments, the fastening laminate may be an integral ear portion of the absorbent article. The carrier at the user's end of a fastening tab may exceed the extension of the spread mechanical fastening patch thereby providing a fingerlift. When the spread mechanical fastening patch is used in a fastening tab, exposed adhesive that may be present in some embodiments between the multiple strands of the spread mechanical fastening patch may be useful for "anti-flagging" or for maintaining the disposable absorbent article in a rolled up state after use. Also when the spread mechanical fastening patch is used as a landing zone or fastening tab, exposed adhesive that may be present in some embodiments between the multiple strands of the spread mechanical fastening patch may be useful to provide a combination of mechanical and adhesive fastening. The fastening laminate made by the methods disclosed herein may also be useful, for example, for disposable articles such as sanitary napkins.

The mechanical fasteners and laminates made according to the present disclosure may also be useful in many other fastening applications, for example, assembly of automotive parts or any other application in which releasable attachment may be desirable.

Some Embodiments of the Disclosure

In a first embodiment, the present disclosure provides a method of making a mechanical fastener, the method comprising:

providing a slit web having mechanical fastening elements and a length in a machine direction, wherein the slit web comprises a plurality of laterally separated interrupted slits that are interrupted by intact bridging regions of the web, wherein the interrupted slits extend in a first direction not parallel to a cross-machine direction, and wherein for at least some adjacent interrupted slits, the intact bridging regions are staggered in a direction transverse to the first direction;

applying tension to the slit web in the machine direction; and spreading the slit web in the cross-machine direction by directing its side edges over two rotating diverging disks to provide a spread mechanical fastening web, wherein the two rotating diverging disks are laterally spaced and have a support surface between them that contacts the slit web during the spreading, and wherein the spread mechanical fastening web comprises multiple strands of the slit web attached to each other at least at some of the intact bridging regions and separated from each other between at least some of the intact bridging regions.

In a second embodiment, the present disclosure provides the method of the first embodiment, wherein the support surface is connected to the two rotating diverging disks.

In a third embodiment, the present disclosure the method of the first or second embodiment, wherein the support surface is flush with the two rotating diverging disks' peripheral surfaces.

In a fourth embodiment, the present disclosure provides the method of the first or second embodiment, wherein the support surface bulges outward beyond the two rotating diverging disks' peripheral surfaces.

In the fifth embodiment, the present disclosure provides the method of any one of the first to fourth embodiments, wherein the side edges of the slit web are held to the diverging disks' peripheral surfaces using continuous belts.

In a sixth embodiment, the present disclosure provides the method of any one of the first to fifth embodiments, wherein the side edges of the slit web are held to the diverging disks' peripheral surfaces using pins.

In a seventh embodiment, the present disclosure provides the method of any one of the first to sixth embodiments, wherein the side edges of the slit web are held to the diverging disks' peripheral surfaces using vacuum.

In an eighth embodiment, the present disclosure provides the method of any one of the first to seventh embodiments, wherein the side edges of the slit web are held to the diverging disks' peripheral surfaces using forced air jets.

In a ninth embodiment, the present disclosure provides the method of any one of the first to eighth embodiments, further comprising heating the spread mechanical fastening web, for example, to anneal the spread mechanical fastening web.

In a tenth embodiment, the present disclosure provides the method of any one of the first to ninth embodiments, wherein the slit web is arranged so that the mechanical fastening elements face away from the support surface.

In an eleventh embodiment, the present disclosure provides the method of the tenth embodiment, wherein the support surface is heated.

In a twelfth embodiment, the present disclosure provides the method of any one of the ninth to eleventh embodiments, wherein heating comprises directing the spread mechanical fastening web onto a rotating heated cylinder.

In a thirteenth embodiment, the present disclosure provides the method of the ninth embodiment, wherein the slit web is arranged so that the mechanical fastening elements face toward the support surface.

In a fourteenth embodiment, the present disclosure provides the method of any one of ninth to thirteenth embodiments, wherein heating the spread mechanical fastening web comprises using non-contact heating.

In a fifteenth embodiment, the present disclosure provides the method of the thirteenth or fourteenth embodiment, wherein the slit web is coated with adhesive on its surface opposite the mechanical fastening elements.

In a sixteenth embodiment, the present disclosure provides the method of any one of the first to fifteenth embodiments, further comprising directing the spread mechanical fastening web onto a high-friction roller.

In a seventeenth embodiment, the present disclosure provides the method of the sixteenth embodiment, wherein the high-friction roller is heated.

In an eighteenth embodiment, the present disclosure provides the method of the sixteenth embodiment, wherein the high-friction roller is chilled.

In a nineteenth embodiment, the present disclosure provides the method of any one of the first to eighteenth embodiments, further comprising directing the spread mechanical fastening web onto a rotating chilled cylinder.

In a twentieth embodiment, the present disclosure provides the method of any one of the first to nineteenth embodiments, further comprising laminating the spread mechanical fastening web to a carrier.

In a twenty-first embodiment, the present disclosure provides the method of the twentieth embodiment, wherein the carrier is a nonwoven web.

In a twenty-second embodiment, the present disclosure provides the method of the twentieth or twenty-first embodiment, wherein the carrier is provided with a layer of an adhesive.

In a twenty-third embodiment, the present disclosure provides the method of the twenty-second embodiment, wherein the spread mechanical fastening web is bonded to the carrier with the adhesive to form a laminate, and wherein the adhesive is exposed between the multiple strands in the laminate.

In a twenty-fourth embodiment, the present disclosure provides the method of any one of the first to twenty-third embodiments, wherein the slit web is spread such that that the width of the spread mechanical fastening web is up to 150 percent greater than the width of the slit web.

In a twenty-fifth embodiment, the present disclosure provides the method of any one of the first to twenty-fourth embodiments, further comprising spreading the spread mechanical fastening web in a cross-machine direction a second time by directing its side edges over a second set of two rotating diverging disks, wherein in the second set, the two rotating diverging disks are laterally spaced and have a support surface between them that contacts the spread mechanical fastening web during the spreading a second time.

In a twenty-sixth embodiment, the present disclosure provides the method of any one of the first to twenty-fifth embodiments, wherein the first direction is the machine direction.

In a twenty-seventh embodiment, the present disclosure provides the method of any one of the first to twenty-sixth embodiments, wherein there is no macroscopic stretch-induced molecular orientation in the slit backing in the cross-direction.

In a twenty-eighth embodiment, the present disclosure provides the method of any one of the first to twenty-seventh embodiments, wherein the multiple strands of the slit web attached to each other at least at some of the intact bridging regions form an angle of less than 90 degrees.

In a twenty-ninth embodiment, the present disclosure provides the method of any one of the first to twenty-eighth embodiments, wherein the mechanical fastening elements are male fastening elements comprising upstanding posts having bases attached to the slit web. The male fastening elements may also comprise caps distal from the slit web.

In a thirtieth embodiment, the present disclosure provides the method of the twenty-ninth embodiment, wherein the width dimension of each of the multiple strands is wider than at least the bases of the upstanding posts.

In a thirty-first embodiment, the present disclosure provides the method of the twenty-ninth or thirtieth embodiment, wherein the caps have loop-engaging overhangs extending beyond the upstanding posts at a non-zero angle to the direction of the interrupted slits.

In a thirty-second embodiment, the present disclosure provides the method of any one of the twenty-ninth to thirty-first embodiments, further comprising providing a thermoplastic backing having multiple rows of the upstanding posts, wherein providing the slit web comprises slitting through the thermoplastic backing between at least some pairs of adjacent rows of the upstanding posts.

In a thirty-third embodiment, the present disclosure provides the method of any one of the first to twenty-eighth embodiments, wherein the slit web has loops.

This disclosure is not limited to the above-described embodiments but is to be controlled by the limitations set forth in the following claims and any equivalents thereof. This disclosure may be suitably practiced in the absence of any element not specifically disclosed herein.

What is claimed is:

1. A method of making a mechanical fastener, the method comprising:
    providing a slit web having mechanical fastening elements and a length in a machine direction, wherein the slit web comprises a plurality of laterally separated interrupted slits that are interrupted by intact bridging regions of the web, wherein the interrupted slits extend in a first direction not parallel to a cross-machine direction, and wherein for at least some adjacent interrupted slits, the intact bridging regions are staggered in a direction transverse to the first direction;
    applying tension to the slit web in the machine direction; and
    spreading the slit web in the cross-machine direction by directing its side edges over two rotating diverging disks to provide a spread mechanical fastening web, wherein the two rotating diverging disks are laterally spaced and have a support surface between them that contacts the slit web during the spreading, and wherein the spread mechanical fastening web comprises multiple strands of the slit web attached to each other at least at some of the intact bridging regions and separated from each other between at least some of the intact bridging regions.

2. The method of claim 1, wherein the support surface is connected to the two rotating diverging disks.

3. The method of claim 1, wherein the support surface is flush with the two rotating diverging disks' peripheral surfaces.

4. The method of claim 1, wherein the support surface bulges outward beyond the two rotating diverging disks' peripheral surfaces.

5. The method of claim 1, wherein the side edges of the slit web are held to the diverging disks' peripheral surfaces using at least one of continuous belts, pins, vacuum, or forced air jets.

6. The method of claim 1, further comprising heating the spread mechanical fastening web.

7. The method of claim 1, wherein slit web is arranged so that the mechanical fastening elements face away from the support surface.

8. The method of claim 7, wherein the support surface is heated.

9. The method of claim 1, wherein the slit web is arranged so that the mechanical fastening elements face toward the support surface.

10. The method of claim 9, wherein the slit web is coated with adhesive on its surface opposite the mechanical fastening elements.

11. The method of claim 1, further comprising directing the spread mechanical fastening web onto a high-friction roller.

12. The method of claim 1, wherein the multiple strands of the slit web attached to each other at least at some of the intact bridging regions form an angle of less than 90 degrees.

13. The method of claim 1, further comprising spreading the spread mechanical fastening web in a cross-machine direction a second time by directing its side edges over a second set of two rotating diverging disks, wherein in the second set, the two rotating diverging disks are laterally spaced and have a support surface between them that contacts the spread mechanical fastening web during the spreading a second time.

14. The method of claim 1, further comprising laminating the spread mechanical fastening web to a carrier.

15. The method of claim 14, wherein the carrier is provided with a layer of adhesive, wherein the spread mechanical fastening web is bonded to the carrier with the adhesive to form a laminate, and wherein the adhesive is exposed between the multiple strands in the laminate.

16. The method of claim 14, wherein the carrier is a nonwoven web.

17. The method of claim 6, wherein heating the spread mechanical fastening web comprises using non-contact heating.

18. The method of claim 1, wherein the first direction is the machine direction.

19. The method of claim 1, wherein the mechanical fastening elements are male fastening elements comprising upstanding posts having bases attached to the slit web.

20. The method of claim 1, wherein the slit web has loops.

* * * * *